United States Patent [19]

Urist

[11] Patent Number: 4,596,574

[45] Date of Patent: Jun. 24, 1986

[54] BIODEGRADABLE POROUS CERAMIC DELIVERY SYSTEM FOR BONE MORPHOGENETIC PROTEIN

[75] Inventor: Marshall R. Urist, Pacific Palisade, Calif.

[73] Assignee: The Regents of the University of California, Berkeley, Calif.

[21] Appl. No.: 609,810

[22] Filed: May 14, 1984

[51] Int. Cl.$^4$ .................. A61F 2/28; A61F 2/32; C07G 7/00

[52] U.S. Cl. ........................ 623/16; 623/22; 424/14; 424/95

[58] Field of Search ............ 424/14, 357, 95; 3/1.9, 3/1.912, 1.913; 623/16, 22, 23

[56] References Cited

U.S. PATENT DOCUMENTS

| | | | |
|---|---|---|---|
| 3,918,100 | 11/1975 | Shaw et al. | 3/1.913 |
| 3,922,155 | 11/1975 | Broemer et al. | 3/1.9 |
| 3,981,736 | 9/1976 | Broemer et al. | 3/1.913 |
| 4,294,753 | 10/1981 | Urist | 260/112 R |
| 4,322,398 | 3/1982 | Reiner et al. | 3/1.9 |
| 4,347,234 | 8/1982 | Wahlig et al. | 3/1.9 |
| 4,365,356 | 12/1982 | Broemer et al. | 3/1.912 |
| 4,455,256 | 6/1984 | Urist | 260/112 R |
| 4,472,840 | 9/1984 | Jefferies | 3/1.9 |
| 4,508,704 | 4/1985 | Simon et al. | 424/14 |

FOREIGN PATENT DOCUMENTS

| | | | |
|---|---|---|---|
| 58-12649 | 1/1983 | Japan | 3/1.9 |
| 59-101145 | 6/1984 | Japan | 3/1.9 |

OTHER PUBLICATIONS

Hench, L. L. et al., *J. Biomedical Mater. Res. Symposium* No. 4, pp. 25–42, "Direct Chemical Bond of Bioactive Glass–Ceramic Materials to Bone and Muscle," (1973).

Primary Examiner—Ronald W. Griffin
Attorney, Agent, or Firm—Kenyon & Kenyon

[57] ABSTRACT

Disclosed is a biodegradable porous ceramic delivery system useful for delivery of bone morphogenic protein (BMP) to viable tissue and to induce formation of new bone therein. The delivery composite is substantially pure BMP in combination with a biodegradable porous ceramic (sintered), e.g. beta-tricalcium phosphate, and may be prepared by admixing the BMP with the porous ceramic material. The composition is implanted in viable tissue where the BMP is slowly released and induces formation of new bone.

25 Claims, No Drawings

BIODEGRADABLE POROUS CERAMIC DELIVERY SYSTEM FOR BONE MORPHOGENETIC PROTEIN

BACKGROUND OF THE INVENTION

This invention was made with Government support under Grant No. DE 02103 awarded by the Department of Health and Human Services. The Government has certain rights in this invention.

This invention relates to systems and methods for delivering bone morphogenetic protein (BMP) to viable bone and other skeletel tissues. More specifically, the invention relates to a delivery system for BMP utilized in bone implants, and comprises a physiologically acceptable, porous ceramics containing substantially pure BMP. The delivery system may thus be applied to defective bone tissue and other viable tissue to induce formation of new bone. The invention also relates to the preparation of such a bone implant system and a method of using the system as a bone implant.

BMP is a relatively low molecular weight protein or proteon implant that is isolated from dentin, bone and other skeletel tissues by chemical extraction and differentiation precipitation. BMP in vitro induces perivascular mesenchymal type cells to differentiate into cartilage and bone by endochrondal ossification. The target of BMP is connective tissue cells (pericytes) surrounding small blood vessels of bone marrow and muscle attachments to bone. BMP may be isolated in relatively pure form by processes described in U.S. Pat. No. 4,294,753 and in copending patent application Ser. No. 260,726 filed May 5, 1981. BMP, and processes for its isolation and more complete purification are further described in Ser. No. 523,606 filed Aug. 16, 1983. The disclosures in said patent and applications are incorporated herein by It is disclosed in the aforementioned patent and patent applications that BMP may be implanted directly into a bone defect where it stimulates differentiation of connective tissue into bone and thereby repairs defects therein. After about six months remodeling is substantially complete, and about 1 gram of bone is produced for each milligram of BMP implanted. Such levels of bone induction have been observed when a relatively high proportion of BMP is initially used in the implant. Otherwise, at lower total BMP levels new bone induction is substantially reduced or no induction at all takes place. For example, when up to 1 mg of BMP was inserted into a mouse muscle pouch, the BMP was rapidly absorbed and did not induce formation of grossly visible deposits of new bone. Moreover, the nature (metabolic rate) of the animal subject under treatment is a major determinant as to the minimum quantity of BMP that will induce new bone formation.

It is therefore, an object of the present invention to develop a delivery system for BMP which increases the yield of bone generation per unit weight of BMP. Another object of the present invention is to provide delivery systems for BMP that minimize acute deleterious inflamatory reactions in implant recipients and are rapidly dissolved and absorbed into the body. A further object is the development of a physiologicaly acceptable biodegradable system which is metabolized so that the regenerated bone eventually will be substantially free of foreign material.

SUMMARY OF THE INVENTION

The present invention provides a BMP delivery system and method that greatly increase the amount of new bone formed by viable tissue in response to a given amount of substantially pure BMP, and new bone so formed which will eventually be substantially free of foreign material. More particularly, the threshold quantity of BMP required to induce new bone formation is substantially reduced and the delivery system for the BMP is removed from the bone by dissolution, phagocytosis or some other natural agency.

It has now been discovered that a delivery system for BMP comprising a composition of a physiologically acceptable, biodegradable porous ceramic containing substantially pure BMP allows the BMP to be delivered on a sustained basis to host tissue, preferably bone tissue, so that enhanced bone formation will be induced for a substantial period. Yet, the delivery system is biodegradable within the viable animal protein and thus eventually removed and eliminated via natural agencies. The porous ceramic may constitute a porous sintered, porous vitreous, or porous glass-like, physiologically acceptable, biodegradable alkali metal salt, alkaline earth metal salt, or transition metal salt. For example, physiologically acceptable, biodegradable, salts include but are not limited to the phosphates, sulfates, carbonates, and silicates of sodium, potassium, calcium, magnesium, manganese, vanadium, iron, copper, zinc, silver, gold, platinum, aluminum, cobalt and the like. The salts are sintered to reduce their solubility in body fluids causing a corresponding reduction in their chemical activity so that the porous ceramic is well tolerated in the body and acute inflamatory reactions are avoided. A preferred ceramic is sintered calcium phosphate, preferably, tricalcium phosphate (TCP). An especially preferred ceramic phosphate is beta tricalcium phosphate (BTCP) having a Ca/P ratio of about 1.5. Porous ceramic for purposes of this invention means any of the foregoing salts that are formed into a sintered or ceramic mass having pores suitable for containing effective amounts lyophilized BMP. Such a ceramic will be biodegradable and physiologically acceptable and preferably non-chelating with respect to the BMP.

The BMP-porous ceramic delivery system of this invention provides, sustained delivery of BMP and causes stimulation of host bed new bone formation for a period believed to be on the order of months, e.g. 30–90 days, or longer. Moreover, the quantity of new bone that is induced for a given amount of BMP implanted in the BMP-porous ceramic delivery system described herein has been found to be significantly higher when compared with new bone formation induced by BMP in the absence of the porous ceramic disclosed herein. For example, as shown herein, a BTCP/BMP implant produced nine times more volume of new bone than BMP alone when implanted in mice for 21 days. The BTCP was rapidly eliminated from the new bone. Thus, the present invention allows for substantially reduced quantities of BMP to be used in a bone implant, and yet results in the induced formation of significant quantities of new bone. Histological sections examined at 21 days after the implantation showed progressive dissolution and absorption of the implant. The observation that the BMP-porous ceramic delivery system of this invention induces formation of large quantities of new bone from smaller quantities of BMP compared to an implant of BMP dispersed in the tissue without porous ceramic carrier sugggests that slow absorption in a locally sustained concentration gradient of BMP enhances the bone morphogenetic response.

DETAILED DESCRIPTION OF THE INVENTION

BMP delivered by the system of this invention induces formation of bone by the host bed connective tissues surrounding the implant and assimilation into existing bone. Other advantages of the BMP-porous ceramic delivery system include, (1) long term proliferation of new bone for substantial reinforcement of the host bone bed, (2) ingrowth of bone into the implant etc. surfaces and interior crevices containing the composition, (3) prevention of loosening of joint implants in young active patients and (4) metabolism and removal of the porous ceramic system after its function has been performed.

An example of the biodegradable porous ceramic useful in the practice of the present invention is BTCP available from Synthos, Miter Corp., Columbus, Ohio or which may be prepared by methods described by Driskell et al., "Calcium Phosphate Restorable Ceramics: a Potential Alternative to Bone Grafting", *Intern. Ass. Dent. Res. Abstracts,* 259:123 (1973); Bhaskar et al., "Biodegradable Ceramic Implants in Bone Electron and Light Microscopic Analysis", *Oral Surgery* 32(2): 336-346 (1971). The physiologically acceptable porous ceramic containing BMP according to the present invention is designed as a biodegradable delivery system. In nature, bone collagen and other high MW bone proteins represent that delivery system for endogenous BMP. For exogenous BMP useful in treatment of patients with endogenous BMP deficiencies it is advantageous to use a non-immunogenic, non-proteinaceous; delivery system. Because the biodegradable porous ceramic is non-immunogenic, the BMP-biodegradable porous ceramic of the invention is a highly efficient delivery system. Furthermore, BMP implanted free, i.e. without a delivery system, in tissues is so rapidly absorbed that large doses are necessary to induce bone formation. In contrast BMP provided in the form of a the BMP-biodegradable porous ceramic delivery system, is effective in microgram doses.

The method for preparing the BMP-porous ceramic delivery system of the present invention, e.g. implant material, comprises introducing a physiologically acceptable biodegradable porous ceramic such as sintered tricalcium phosphate to an aqueous BMP solution and causing the BMP to become entrapped in the ceramic's pores by evaporating the solvent freeze drying it, or otherwise allowing the ceramic to absorb BMP, which will form the desired system. The most effective weight ratios of porous ceramic to BMP may be determined empirically and the preferred range is at least 1:100 to about 1:1. Similarly, effective dosages are determined by the characteristics of the recipients and the objective of the treatment. The porous ceramic delivery system may be pre-formed by placing the powdered salts into the a mold of the desired shape for implantation, and then firing the salt in a kiln or electric furnance to sinter the salt or otherwise convert it to a solid, unitary porous mass. Generally, this method forms the active delivery system of the invention. Additives or supplements may be included in admixture with the BMP and porous ceramic, each for its own particular function. For example, there may also be included in the system, radioopacifying agents, antibiotics, prosthesis devices, and examples of such additives or supplements include the following: radioopacifying agents (barium sulfate) and antibiotics (gentamyicin or silver sulfate). Such additives have been known and used in connection with bone cement materials. See, for example, *J. Bone Joint Surg.,* 63A;798, 1981, "The Depot Administration of Penicillin G and Gentamyicin in Acrylic Bone Cement", Hoff et al.,; and, *Clin. Orthop.,* 169: 264-268, 1982, "Silver Antibacterial Cement Comparison with gentamycin in experimental osteomyeolitis", Dueland et al. The proportions of the additive to be used are well known. In preferred embodiments, the biodegradable porous ceramic delivery system is formed into a rod, plate, flake or otherwise shaped as desired. It is also contemplated the the BMP-porous ceramic delivery system of the present invention be used in combination with prosthesis devices, e.g. as a coating or impregnate for synthetically constructed bone material, such as an artificial hip.

BMP may be prepared in powder form as set forth in the above-referenced patent and patent applications. Either purified BMP or its co-precipitate with tricalcium phosphate can be used with the porous ceramic to form the delivery system of this invention. The co-precipitate of BMP and tricalcium phosphate alone, however, does not constitute the BMP-biodegradable porous ceramic delivery system of the invention.

The BMP-biodegradable porous ceramic delivery system described herein has applications in enhancing bone repair in orthopedic reconstructive operations.

The literature on biodegradable drug delivery systems has been reviewed in detail by Pitt et al. (1980). Pitt, Colin G., Marks, Thomas A., Schindler, Anton. "Biodegradable Drug Delivery Systems Based on Aliphatic Polyesters: Application to Contraceptives and Narcotic Antagonists." Published by Academia Press, Inc. 1980, for the National Institute on Drug Abuse.

In the absence of BMP, induced bone formation is not known to occur in response to implants of any of the presently known porous ceramics. In the presence of BMP in the form of a BMP-biodegradable porous ceramic delivery system new bone formation is induced de novo in either extraskeletal or intraskeletal sites. Morphologically, the process is similar in response to BMP in an endogenous delivery system such as demineralized bone matrix proteins as described in previous publications. Urist, M.R., *New Bone Formation Induced in Post fetal life by Bone Morphogenetic Protein.* Edited by R. Becker. Springfield, Ill. Thomas and Co. 1981. pp.406-734.

The invention will be further illustrated by the following example.

EXAMPLE

Preparation of a bBMP/BTCP System and Use Thereof

A 2 g sample of BTCP was immersed in an aqueous solution of bBMP, 1 mg/ml of sterile distilled water for 24 hours at 28° C., with stirring. The bBMP was bovine bone marrow protein prepared from bovine cortical bone by separating the BMP from a 14K alpha carboxyglutamic acid rich protein in accordance with the method disclosed in Urist et al., "Purification of Bovine Bone Morphogenic Protein (bBMP) by Hydroxyapatite Chromatography", *Proc. Nat. Acad. Sci. (USA)* 81: 371-375 (1983), and the above-described patents. The bBmp was entrapped in the pores of the BTPC by lyophilization. Samples (20 mg) of the BTCP/bBMP, (19 parts BTCP to 1 part bBMP) system were implanted in muscle pouches in the thighs of adult Swiss Webster mice. The recipients were sacrificed at intervals of 1, 2, 4, 8, and 21 days, and the implants examined by correlated microradiographic and histological methods. For controls, 20 mg samples of BTCP without bBMP and similar samples of unbound lyophilized bBMP were implanted in the same species of mice and excised at the same intervals of time. The quantity of new bone was measured in terms of $mm^3$ per mg of implanted bBMP by histomorphometic methods.

On days 1 and 2 post implantation, the BTCP/bBMP implants were encased in an envalop of acute inflammatory cells. On day 4, the envelop increased in thickness and the polymorphonuclear leucocytes were fewer while the small round cells and plasma cells were greater in number. The interior of the implants was infiltrated with macrophages containing phagocytosed particles of BTCP. Before day 4, there were little or microscopic differences in the cellular reactions to BTCP/bBMP and BTCP control implants. By day 8, the BTCP/bBMP implants were infiltrated with proliferating spindle shaped and hypertrophied mesenchymal cells surrounding islands of proliferating cartilage. In contrast, the BTCP controls were further encased in a subacute and chronic inflammatory tissue including small round cells, macrophages and multinuclear giant cells. By day 12, the BTCP/bBMP implants contained large quantities of cartilage, with small foci of chondroid, osteoid, and newly calcified woven bone. photomicrograph, hemotoxylin, (eosin and azure II stain x 250) stained new cartilage chondroid, and chondoosteoid differentiation induced by BTCP/bBMP, at 8 days after implantation in mouse thigh showed proliferating mesenchymal type cells cartilage and remnants of the porous matrix of BTCP in which BMP was incorporated. By day 21, more than half of the BTCP was absorbed from both BTCP/bBMP and BTCP control implants. The latter were disintergerated and partially phagocytosed by large multinucleated cells and macrophages, and encapsulated in fibrous connective tissue. The BTCP/bBMP implants were replaced by new bone and bone marrow tissue with small inclusions of calcified cartilage. Photomicrographs of ossicle with a core of undecalcified BTCP containing bBMP show a demineralized BTCP/bBMP structure, new bone, bone marrow and an envelope of fibrous tissue and muscle. By day 21, the quantity of new bone produced by BTCP/bBMP (expressed in $mm^3$ per mg of bBMP) was nine times greater than that from the implants of unbound lyophilized bBMP.

The BTCP/bBMP implant induces bone formation and constitutes a delivery system for bBMP which is comparable to natural demineralized bone matrix in muscle of subcutis. Implants of hydroxyapatite and other calcium phosphates, including BTCP, have been implanted in heretotopic sites for many years without any evidence of induced bone formation. Coprecipitates of calcium phosphate and BMP inside of diffusion chambers, induce formation of new bone on the outside. The same coprecipitates on the outside of the diffusion chambers incite only an acute deleterious inflammatory reaction. In the present invention, the use of a sintered calcium phosphate ameliorates such an inflammatory reaction and the absorbed bBMP induces ingrowth of migratory mesenchymal-type cells. The net result is a blockade of the systemic cell mediated inflammatory cell reaction and promotion of the local morphogenetic response leading to cartilage and bone cytodifferentiation. Hydrated tricalcium phosphate (Ca/P=1.5) is an intermediate form in the deposition of the final form (Ca/P=1.66) of the bone mineral.

What is claimed is:

1. A composition comprising a physiologically acceptable, biodegradable porous ceramic containing bone morphogenic protein (BMP).

2. A composition according to claim 1, wherein the physiologically acceptable, biodegradable porous ceramic is composed of a salt having a cation selected from the group consisting of physiologically acceptable alkali metals, alkaline earth metals, and transition metals and an anion selected from the group consisting of phosphate, sulfate, carbonate and silicate.

3. A composition according to claim 2, wherein the porous ceramic has a sintered, vitreous or glass-like form.

4. A composition according to claim 3, wherein the cation is selected from the group consisting of sodium, potasium, calcium, magnesium, manganese, vandium, iron, copper, zinc, silver, gold, aluminum, cobalt and platinum.

5. A composition according to claim 1, wherein the physiologically acceptable, biodegradable porous ceramic is a sintered mass of tricalcium phosphate (TCP).

6. A composition according to claim 1, wherein the physiologically acceptable, biodegradable porous ceramic is a sintered mass of beta tricalcium phosphate (BTCP).

7. A system for delivering bone morphogenic protein (BMP) to viable tissue and inducing formation of new bone therein, comprising:
a physiologically acceptable, biodegradable porous ceramic containing substantially pure bone morphogenic protein (BMP).

8. A delivery system according to claim 7, wherein the ceramic is sintered, porous beta tricalcium phosphate (BTCP).

9. The delivery system according to claim 8, wherein the weight ratio of BMP to sintered porous BTCP is at least about 1 part BMP to about 100 parts sintered porous BTCP.

10. A delivery system according to claim 9, wherein the sintered porous beta tricalcium (BTCP) has a Ca/P ratio of about 1.5.

11. A delivery system according to claim 10, wherein the weight ratio is in the range of about 1 part bone morphogenic protein (BMP) to 19 parts sintered porous BTCP.

12. A delivery system according to claim 9, wherein the sintered porous beta tricalcium phosphate (BTCP) has a Ca/P ratio of about 1.66.

13. A delivery system acocrding to claim 7, further comprising a radioopacifying agent contained in said ceramic.

14. A delivery system according to claim 7, further comprising an antibiotic contained in said ceramic.

15. An artificial appliance comprising a prosthesis bone device in combination with a delivery system according to claim 7.

16. A method for inducing formation of new bone in viable tissue, comprising:
implanting in said viable tissue a delivery system of a physiologically acceptable, biodegradable porous ceramic containing substantially pure BMP wherein the weight ratio is at least about 1 part BMP to about 100 parts porous ceramic.

17. A method for preparing a delivery system composite for delivering bone morphogenic protein (BMP) to viable tissue and inducing formation of new bone therein, comprising:

contacting a physiologically acceptable, biodegradable porous ceramic with a liquid containing substantially pure BMP and removing said liquid therefrom so that an effective amount of BMP is entrapped in the porous ceramic.

18. A method according to claim 17, wherein the porous ceramic is composed of a salt having a cation selected from the group consisting of a physiologically acceptable alkali metal, a physiologically acceptable alkaline earth metal, and a physiologically acceptable transition metal; and an anion selected from the group consisting of phosphate, sulfate, carbonate and silicate.

19. The method according to claim 18, wherein the cation is selected from the group consisting of sodium, potassium, calcium, magnesium, manganese, vanadium, iron, copper, zinc, silver, gold, aluminum, colbalt, and platinum.

20. A method according to claim 17, wherein the porous ceramic is a sintered mass of TCP.

21. A method according to claim 20, wherein the sintered mass is beta tricalcium phosphate (BTCP) which has a Ca/P ratio of about 1.5.

22. A method according to claim 21 wherein the weight ratio is in the range of about 1 part BMP to 19 parts BTCP.

23. A method according to claim 22 wherein the delivery system, further comprises an antibiotic contained in said ceramic.

24. The method according to claim 22 wherein the delivery system composite, further comprises a radioopacifying agent contained in said ceramic.

25. A method for preparing a prosthesis for implanting, which comprises:

providing a bone morphogenic protein (BMP) delivery system of a physiologically acceptable, biodegradable porous ceramic containing substantially pure BMP on at least a portion of the prosthesis.

* * * * *